United States Patent
Thistle et al.

(10) Patent No.: US 8,292,946 B2
(45) Date of Patent: Oct. 23, 2012

(54) MEDICAL IMPLANTS WITH LIMITED RESISTANCE TO MIGRATION

(75) Inventors: Robert Thistle, Bridgewater, MA (US); Mark Wolfson, Wellesley, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 913 days.

(21) Appl. No.: 11/258,278

(22) Filed: Oct. 25, 2005

(65) Prior Publication Data

US 2007/0093888 A1 Apr. 26, 2007

(51) Int. Cl.
*A61F 2/06* (2006.01)
(52) U.S. Cl. .................................... 623/1.15
(58) Field of Classification Search .............. 623/1.13, 623/1.14, 1.16, 1.18, 1.36, 1.49, 1.51, 1.53, 623/1.54
See application file for complete search history.

(56) References Cited

U.S. PATENT DOCUMENTS

| | | | |
|---|---|---|---|
| 4,655,771 A | 4/1987 | Wallsten | |
| 5,052,998 A | 10/1991 | Zimmon | |
| 5,397,355 A | 3/1995 | Marin et al. | |
| 5,540,712 A * | 7/1996 | Kleshinski et al. | 623/1.19 |
| 5,681,346 A | 10/1997 | Orth et al. | |
| 5,709,704 A * | 1/1998 | Nott et al. | 606/200 |
| 5,713,917 A | 2/1998 | Leonhardt et al. | |
| 5,720,776 A | 2/1998 | Chuter et al. | |
| 5,733,325 A | 3/1998 | Robinson et al. | |
| 5,807,404 A * | 9/1998 | Richter | 623/1.16 |
| 5,824,053 A | 10/1998 | Khosravi et al. | |
| 5,843,164 A | 12/1998 | Frantzen et al. | |
| 6,168,616 B1 | 1/2001 | Brown, III | |
| 6,258,026 B1 * | 7/2001 | Ravenscroft et al. | 600/200 |
| 6,342,063 B1 | 1/2002 | DeVries et al. | |
| 6,344,056 B1 * | 2/2002 | Dehdashtian | 623/1.35 |
| 6,485,507 B1 | 11/2002 | Walak et al. | |
| 6,517,573 B1 | 2/2003 | Pollock et al. | |
| 6,585,758 B1 | 7/2003 | Chouinard et al. | |
| 6,589,275 B1 * | 7/2003 | Ivancev et al. | 623/1.15 |
| 6,994,092 B2 | 2/2006 | Van der Burg et al. | |
| 2001/0039450 A1 * | 11/2001 | Pavcnik et al. | 623/1.24 |
| 2003/0220683 A1 | 11/2003 | Minasian et al. | |
| 2004/0167605 A1 | 8/2004 | Elliott | |
| 2005/0277977 A1 | 12/2005 | Thornton | |

OTHER PUBLICATIONS

S. W. Robertson et al., Mechanical fatigue and fracture of Nitinol, 57 Int'l Materials Reviews 1-36 (2012).*

* cited by examiner

*Primary Examiner* — Gary Jackson
*Assistant Examiner* — Christopher Schubert
(74) *Attorney, Agent, or Firm* — Vidas, Arrett & Steinkraus

(57) ABSTRACT

An implant adapted to be retained in a body lumen includes a barb for engaging the lumen wall. The barb includes a yieldable element adapted to yield in response to a force, above a predetermined limit, tending to cause migration of the implant. The barb may comprise a shape memory material adapted to change shape when the material undergoes a stress induced phase change and thereby to disengage from the lumen wall.

9 Claims, 3 Drawing Sheets

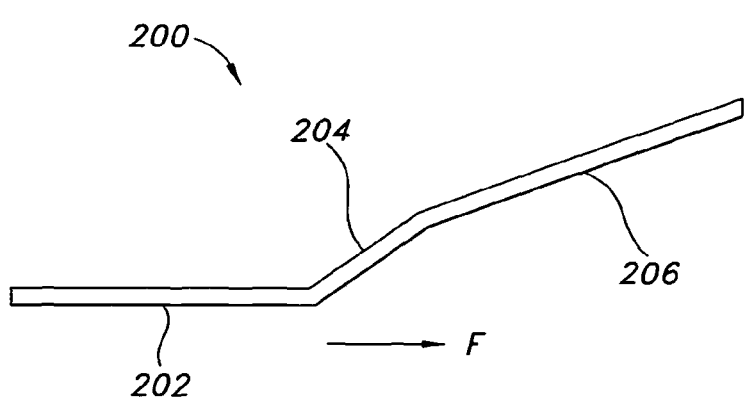
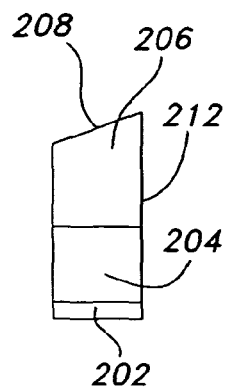
FIG. 4A  FIG. 4C
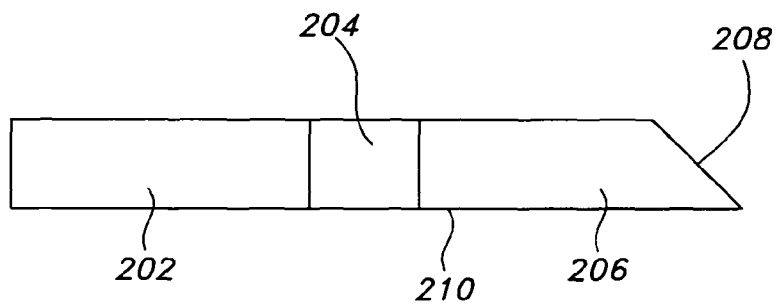
FIG. 4B
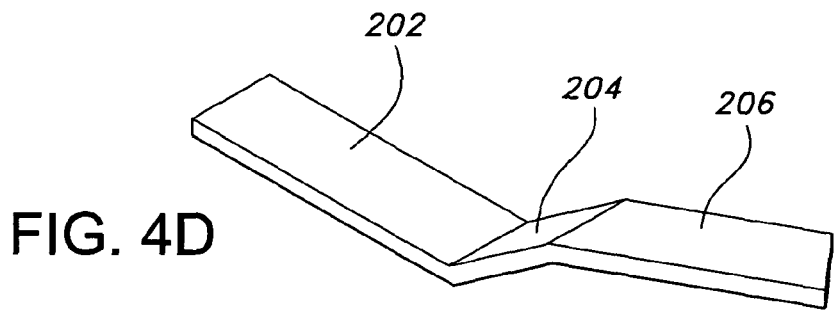
FIG. 4D
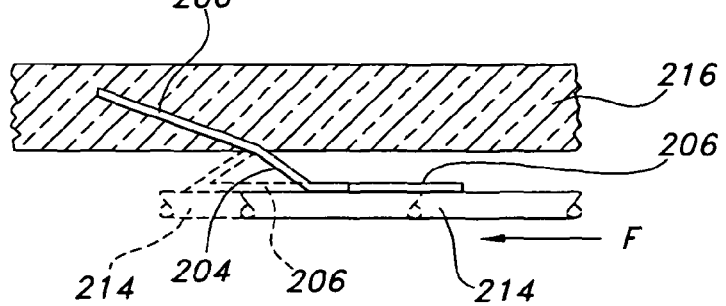
FIG. 4E

MEDICAL IMPLANTS WITH LIMITED RESISTANCE TO MIGRATION

FIELD OF THE INVENTION

This invention relates generally to medical implants which include one or more barbs that engage a body lumen and resist forces tending to cause migration of the implant.

BACKGROUND OF THE INVENTION

Medical implants may provide, for example, unobstructed conduits through a blood vessel in the area of a stenosis. An implant may also be used to treat a vascular aneurysm, for example, by removing pressure on a weakened part of an artery so as to reduce the risk of rupture. A variety of medical devices have been provided with barbs which engage a lumen wall in which the device is implanted and which assist in resisting migratory movement of the device. Such implants are commonly adapted for endoluminal delivery to the deployment site.

The use of shape-memory materials in medical applications is well known. Shape memory materials are materials which can undergo a reversible change from a first "remembered" shape to a second shape.

Nitinol nickel-titanium alloys and doped nickel-titanium alloys (hereafter referred to collectively as Nitinol) are well known as shape memory materials which are used in many medial devices. Nitinol, when heat treated in accordance with known techniques, attains a first "remembered" shape in which it is in an austenitic state. In that state, the material is elastic or super elastic. Nitinol can undergo a reversible phase change, however, from the austentitic state to the martensitic state, in which it is pliable (like cooked spaghetti) and inelastic. This change may be temperature induced or stress induced.

SUMMARY OF THE INVENTION

An implant adapted to be retained in a body lumen includes a barb for engaging the lumen wall. The barb comprises a first element adapted to be associated with the implant. By "associated" is meant the first element is attached to or is a part of the implant. The barb also comprises a second element formed from an elastic material, which yields when a predetermined stress level is exceeded, or from a shape memory material which is adapted to undergo a stress induced phase change when a predetermined force is exerted on the barb's second element. In either case, the barb is disengaged from the lumen wall when that barb element yields. More specifically, the barb has a predetermined force limit to resist force along the length of the implant, such that when the force limit is exceeded, the barb yields to the force and releases the implant's engagement from the lumen wall and thus prevents damage to the lumen wall. When the barb comprises a shape memory metal, it may be designed to undergo a phase change and, in doing so; yield and permit longitudinal movement of the implant. By virtue of the stress induced phase change of the second element, the barb exhibits a first shape when the material is in a first phase and the force is less than the force limit. It exhibits a second shape when the material is in a second phase and force on the barb exceeds the force limit. When the second element is in its first shape, the second element engages an inside of the body lumen. The barb may also be adapted to return to its original pre-yield (and lumen engaging) state. In the case of a shape memory material, this implies a return to the austenitic and lumen engaging shape when the excessive force is removed. In this way, the barb may re-engage the lumen wall and resume resisting migration of the implant in the body lumen.

The Detailed Description which follows may be better understood when read in conjunction with the accompanying figures, in which:

BRIEF DESCRIPTION OF THE DRAWINGS

FIG. 4A is a side view of an exemplary barb which may be incorporated in an implant such as that shown in FIGS. 1-3;

FIG. 4B is a top view of the barb shown in FIG. 4A;

FIG. 4C is an end view of the barb shown in FIG. 4A;

FIG. 4D is a perspective view of the barb shown in FIG. 4A; and

FIG. 4E is a longitudinal view of a stent with an exemplary barb inside a vessel.

DETAILED DESCRIPTION OF THE INVENTION

Figure 1:
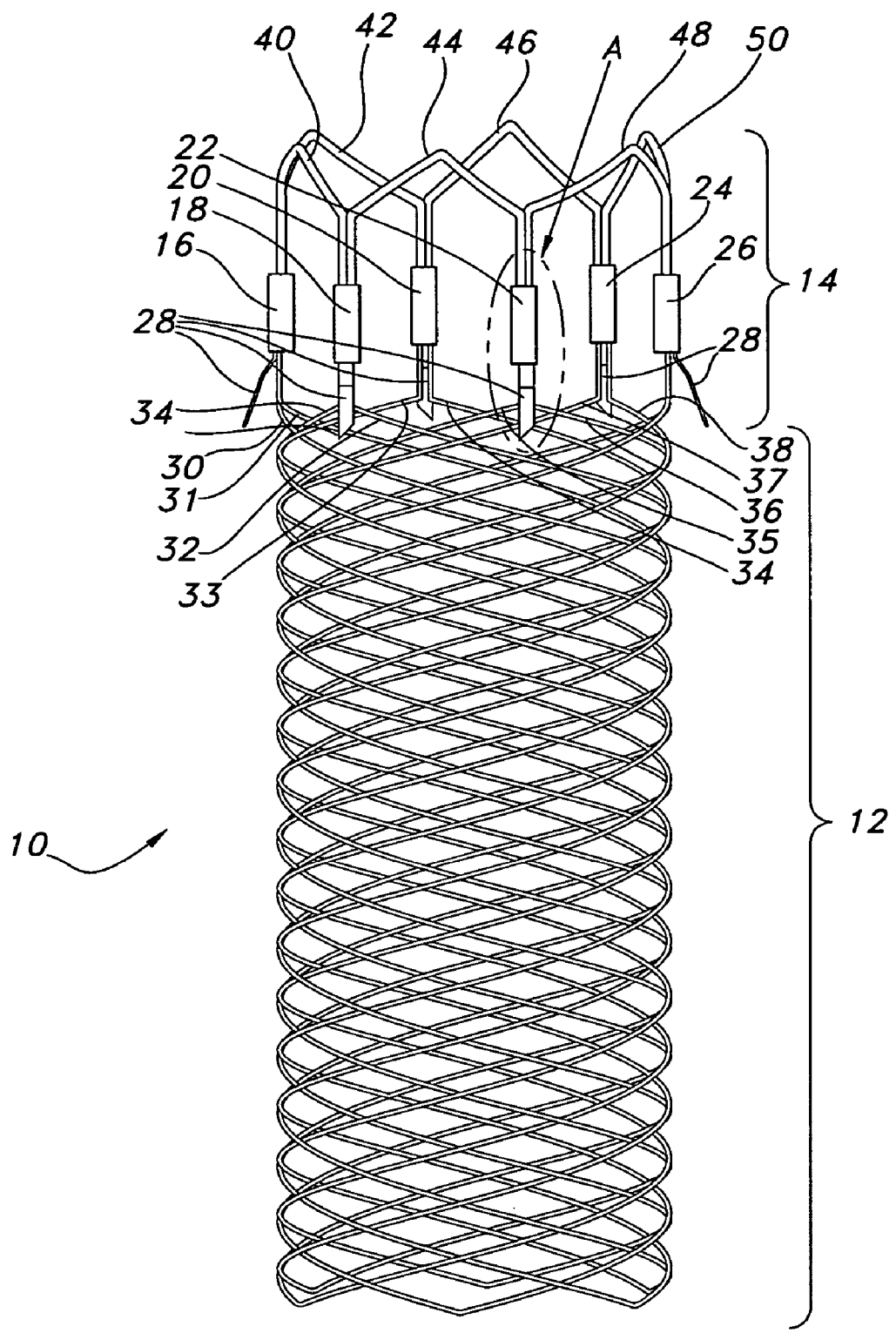
FIG. 1 is a perspective view of a stent having barbs as disclosed herein.

Implants as disclosed herein include a barb adapted to engage the wall of a lumen in which the implant is located. When the barb engages the wall of a lumen in this configuration, the barb resists longitudinal movement of the implant and limits migration of the implant. When forces within the lumen exceed a predetermined force limit, the barb yields to disengage from the lumen wall. This may be accomplished with a barb comprising stainless steel, for example, by appropriate selection of alloy properties and geometry to provide a barb which resists yielding up to a pre-determined force limit and then yields (elastically or inelastically) to permit the barb to disengage before damaging the lumen wall with which it is engaged. The design of such a barb is well within the skill of those familiar with material properties and the designs of medical devices.

A barb may also be comprised of a shape memory material such as Nitinol that may yield by undergoing a stress induced phase change by which it releases its engagement from the lumen wall. When the excessive force is removed, the barb may return to its pre-excessive force condition and re-engage the lumen wall. Materials other than Nitinol (and the entire family of nickel-titanium alloys known as Nitinol) which undergo such stress-induced phase change may also be used and such materials are referred to herein as "shape memory materials."

Implants which may incorporate such barbs include, for example, a vena cava filter or a stent used to treat an abdominal aortic aneurysm (AAA) or a stenosis. The stent may be, for example, a wire stent, a laser cut tube stent, or a stent made of stainless steel, and it may be self expanding or balloon expandable. Such barbs may also be included in other implants which have a stent-like structure for which migration after implantation is sought to be minimized, but in which damage caused by excessive force within the body lumen also is sought to be minimized. The body lumen in which a device of the present invention may be implanted includes any body lumen in which such devices may be typically implanted to perform a wide range of medical functions. In the AAA application, the body lumen is at least one artery, such as the aorta, or the aorta and one or both iliac arteries. Exemplary stent configurations, suitable for this and other applications and in which such barbs can be incorporated, are well known. By way of example only, a few such configurations are described more fully in U.S. Pat. No. 6,585,758-Chouinard et al.

In accordance herewith, one or more barbs incorporated with such an implant is adopted to yield (by elasticity or by a stress induced phase change) to a disengaged state, when a pre-determined force, that might cause migration of the implant, is exceeded. At least a part of one such barb may comprise a shape memory material, such as a Nitinol alloy, in which case disengagement may occur upon a stress-induced phase change.

As mentioned above, as used in medical applications, Nitinol transitions from an austenitic state in which it is superelastic, to a martensitic state in which it is very easily deformable. While that transformation may also be temperature-induced, as used herein the shape memory metal barb is specifically designed and heat-treated to undergo a stress-induced phase transformation. In addition, the elasticity and stiffness of the shape memory metal barb may be controlled by the chemical composition of the alloy comprising the barb, as well as its geometric designs.

Typically, a Nitinol barb and the implant with which it is associated may be cooled to 0° C. or below, at which temperature it is in the martensitic state. This facilitates loading the barb and the implant to which it is coupled into a delivery catheter adapted to facilitate endoluminal delivery of the implant. By the time it is delivered to a desired body location, the barb assumes body temperature, at which it is austenitic and is in its desired final stress-free shape.

By selective design of the relative elasticity of a stent and a barb by which a stent is affixed to a body lumen, and by selective design of the barb so that it yields when force on the implant exceeds a predetermined force limit, the barb's affixation to the body lumen is released when a force on the implant exceeds some predetermined or preselected force limit, which may correspond, when a plurality of such barbs are used, to the aggregate force limit on all such barbs incorporated in the implant. The sum of the force limits on each of the barbs may correspond to the force limit of the implant.

Features and characteristics of barbs can be varied to change the amount of anchoring support provided under certain conditions. The amount of anchoring support (e.g. the stress limit of a barb by which a stent is anchored) to be provided by a barb can be optimized and selected to suit the indications of the particular situation and the characteristics of the implant to which such barbs are coupled. Multiples of such barbs may also be used alone or together with conventional barbs, with the migratory force limit based on the aggregate effect of all of the barbs, i.e., the sum of the force limits of each of the barbs equals the force limit of the implant.

The amount of anchoring support to be provided by a barb or a combination of barbs can be predetermined in the design phase of the barb by design choice of barb thickness or cross sectional dimensions, barb length, barb elasticity (including its yield point) and the angles of various segments of each barb, all of which depend in turn on barb geometry, alloy composition and heat treating conditions. The selection of individual parameters within these variables to achieve the desired amount of force the barb resists before yielding is well within the skill of those routinely involved in the design and manufacture of other Nitinol medical devices. Moreover, the barb or barbs designed to yield in response to excessive force may also be of composite construction, that is they may comprise different materials of construction. For example, Nitinol may comprise one section, element, or part of the barb with that section or element being designed as otherwise disclosed herein, and an associated second section, element, or part may comprise some other material of construction. Moreover, the second section, element, or part may be a part of the barb which is attached to the implant or may actually be a part of the implant itself.

When a barb as otherwise described herein (or at least the barb element comprised of a shape memory material) is comprised of Nitinol, the Nitinol element should be designed to remain in the austenitic phase within a predetermined range of force so that the design stress point, at which the barb disengages from the inside of the body lumen, substantially coincides with the force level at which the material undergoes a stress induced phase change from the austenitic to the martensitic phases.

The material of construction of the barb and the geometry of the barb (particularly that part of the barb designed to yield as described herein) are design considerations that may be used to impart to a barb as disclosed herein the desired engaging, releasing, disengaging, flip-back property, and re-engaging properties and functions described herein.

If, for example, the design limitations of a stent or a filter are such that it should withstand an axial force (i.e., a force that might cause migration of the stent or filter) of about four pounds before yielding to permit some longitudinal movement of the stent or filter, one or more barbs by which the stent or filter is affixed in a body lumen may be designed to yield (or release or flip back) at a total of about three pounds, or about three-and-a-half pounds of force, i.e. with a predetermined safety margin of about one-half to one pound. By way of further example, if the implant includes two such barbs, the pre-selected force limit of the affixing/yielding element in each of the barbs may be about one half of three to three and a half pounds and the geometry and the design of material properties of the barbs to be attached to the stent or filter may be selected accordingly. In this way, the aggregate of the pre-selected barb force limits may be adapted to correspond to the pre-selected implant axial (and potentially migratory-inducing) force limit.

While the stress release barb otherwise described herein may be secured to or associated with a wide variety of medical implants in various ways, such a barb and how it is incorporated in an aortic stent will be specifically disclosed herein by way of example. Referring to FIG. 1, there is shown an aortic stent 10 including an aortic section 12, comprised of helically wound pluralities of stent elements. The stent elements may be filaments of a mesh stent as disclosed for example in U.S. Pat. No. 4,655,771-Wallsten. At the upper end of aortic section 12, its stent elements connect with an upper subsection 14 designed to be retained in a healthy portion of an artery, typically at the intersection with the renal arteries, through crimp tubes 16, 18, 20, 22, 24 and 26 which secure the mating ends of aortic section 12 and upper subsection 14. Upper subsection 14 may also be referred to as a renal section. Typically, the aortic stent itself would be covered by a graft (not shown in these figures) for purposes of bypassing an aneurysm downstream of such a healthy section. In the exemplary stent shown in FIG. 1, upper subsection 14, which provides openings to the renal arteries, includes barbs 28, 30. In this exemplary embodiment, upper subsection 14 comprises six open hexagonal cells defined by wire segments 40, 42, 44, 46, 48 and 50. One or more of the wire segments 40, 42, 44, 46, 48, and 50 may be considered as one or more second stent elements. As described in more detail below, wire segments 40, 42, 44, 46, 48, and 50 are secured in this embodiment by crimp tubes 16, 18, 20, 22, 24, and 26, respectively.

While stress relief barbs as otherwise disclosed herein may be associated with endoluminal stents or other implants in various ways, in this exemplary design embodiment, they are secured at the intersection of aortic section 12 and upper subsection 14 by crimp tubes 16 and 26. Additional barbs may also be secured in other crimp tubes. In an alternative embodiment, the barbs may be attached to the stent or other implant using an attachment mechanism other than a crimp tube. In yet another alternative embodiment, the barbs may comprise an integral part of the stent or implant.

Figure 2:
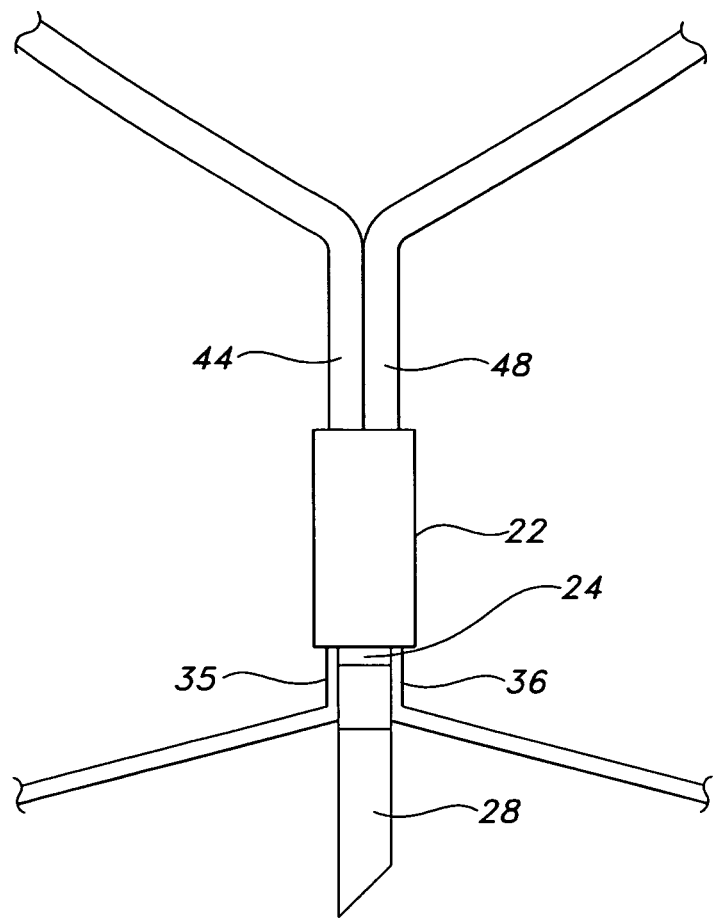
FIG. 2 is a detail view of an Area A of the stent and barb shown in FIG. 1.
Figure 3:
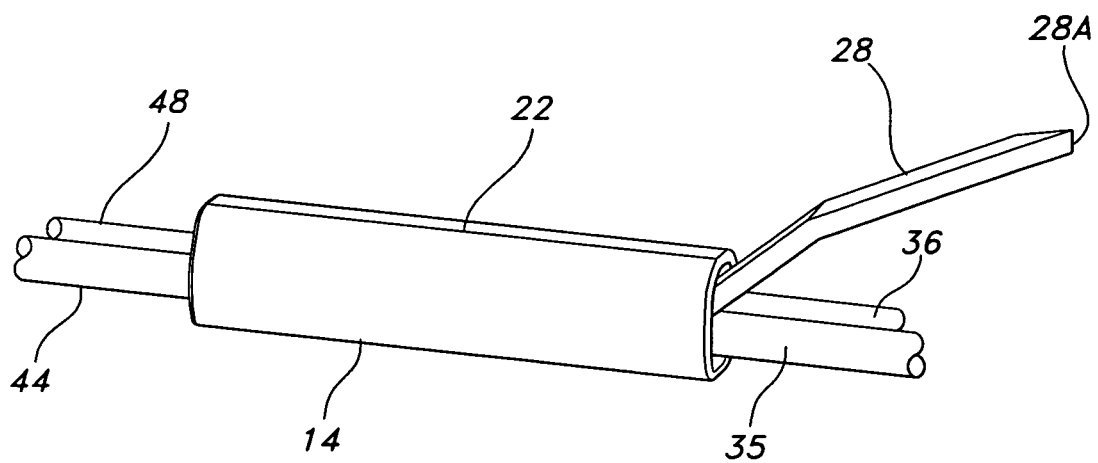
FIG. 3 is a perspective detailed view of Area A in FIG. 1.

For a better understanding of how barb 28, for example, is proposed to be secured to aortic section 12 and upper subsection 14 in this exemplary embodiment, reference may be made to FIG. 2 which is a detailed side view of the Area A in FIG. 1 looking in the direction indicated by arrow A. The design and relationship of crimp tube 22 to barb 28 and upper wire ends 44 and 48 of two wire segments that form upper sub-section 14 and lower ends 35 and 36 of two of the wires forming the mesh of aortic section 12 (a plurality of stent elements) may also be seen in the perspective view of the detail of Area A, shown in FIG. 3. In FIGS. 2 and 3, wire ends 44 and 48 (comprising a second stent element) are both shown along with lower wire ends 35, 36 (comprising terminal portions of two of the wires of the plurality of stent elements forming the mesh stent of aortic section 12) which may be continuations of segments of 44 and 48 of upper sub-section 14. Respectively, these various wire segments may be secured to one another by crimp tube 22 in which is also entrapped barb 28 as seen in more detail in FIG. 3. Tip 28A of barb 28 is the element designed to engage the wall of the lumen in which the stent is implanted. Crimp tube 22 may secure these various wire segments and the barb by means of mechanical crimping or by welding, chemical adhesive, shrink fit, or other such means as may be devised by those in the art, or any combination thereof.

Alternatively, or in addition to downstream facing barbs, as shown in FIG. 1, one or more barbs, as disclosed herein, may be placed to face upstream in order to prevent migration of the stent due to upstream forces. Such upstream forces may be caused by movements of the patient's body over time. As with downstream facing barbs, upstream facing barbs may be placed above and/or below the renal arteries.

In yet another alternative embodiment, one or more barbs may be associated with stent elements at a healthy portion of the aorta just above the iliac bifurcation to provide still further fixation of the stent at another healthy portion of the aorta. Such barbs may also face upstream or downstream in any or all of the combinations described above regarding the placement of barbs at healthy portions of the aorta.

In yet another alternative embodiment (not shown) a barb may be inserted into both ends of crimp tube 26. In this alternative embodiment, one barb and its tip may be aligned to prevent migration of the stent in one direction while the other barb and its tip may be aligned to prevent migration of the stent in the other direction. That is, the two barbs may be aligned to prevent migration in respectively opposite directions.

Still further, the barb or barbs as described herein may be formed as an integral part of the implant itself. For example, a tubular stent made by laser cutting a Nitinol tube may include an element shaped and heat treated such that the element thus shaped and heat treated comprises a shape memory barb element as otherwise disclosed herein.

A test barb, as may be adapted for use in a medical implant such as that shown in FIGS. 1-3, is shown in more detail in FIGS. 4A-4D. A Barb 200, as shown in those figures was formed from a Nitinol alloy strip having about 55% Ni, and 45% Ti. This strip was about 0.007" thick, about 0.034" wide, and was heat treated at about 500° C. The overall length of the ribbon before being bent into its final shape was about 0.269±0.02". Barb 200 has three segments, 202, 204, and 206. First barb segment 202, corresponding to a segment that may be designed to be secured to the stent by being captured in crimp tube 26 (as seen in the previous figures) was about 0.110±0.002" long. At an end of segment 202, barb 200 is bent at an angle of about 33±3 degrees to form segment 204, which is about 0.050" long. At an end of segment 204, barb 200 is bent at an angle of about 20±3 degrees, with respect to segment 202, to form second barb element 206, which is about 0.125" long. Referring to FIG. 4B, the end 208 of segment 206 is cut at an angle of about 45°±3° relative to side 210 of barb 200. Referring to FIG. 4C, the top of segment 204 is 0.027" above the top of segment 202 and the peak of segment 206 is about 0.043" above the top of segment 204. Also referring to FIG. 4C, end 208 is cut at an angle of about 45° relative to side 212 of barb 200 and end 214 is cut at an angle of about 90° relative to side 212.

In this test barb, the entire barb was formed of Nitinol. In other embodiments, only third segment 206 need necessarily comprise a yieldable material. In still other embodiments second and third segments 204 and 206 may be formed of the yieldable element of the barb.

In a test of a barb 200 as shown in FIGS. 4A-4D, strain increased linearly as a force F, substantially parallel to the longitudinal axis of the stent and to the sides and top of barb 200 was increased from 0 pounds to about 0.5 pounds, while the Nitinol comprising the barb remained austenitic. When force F exceeded about 0.5 pounds, (typically as that force approaches 0.6 pounds) the exemplary barb, began a transition to its martensitic phase, resulting in a highly non-linear relationship between force and strain and significant deformation of segments 204 and 206 in the direction of force F. Barb 200 returned to its starting configuration when force F was removed, i.e. the Nitinol barb returned to its original shape and austenitic phase.

FIG. 4E illustrates how a barb as described herein may change shape when it yields under the influence of a force F at or about its predetermined stress limit. Referring to FIG. 4E, a stent 214 is shown positioned inside the lumen of a vessel 216. Stent 214 includes barb 200 which is shown engaged in the interior surface of vessel 216. Arrow F indicates the direction of the direction of a force imposed on stent 214. When force F exceeds the yield limit of barb 200, barb 200 yields to permit movement of stent 214 to the position of the respective elements shown in phantom, namely stent 214 and barb 200.

In a similar manner, others may design similar barbs which deform at some predetermined stress either elastically or by a stress induced phase change. Particularly when such barbs are comprised of a shape memory metal, they may return to their engaging position when the stress is removed. And similarly, others may design a wide variety of medical implants, particularly endoluminal devices, with which one or more such barbs may be associated to provide engagement and resistance to migrating force up to a preset limit and then to release engagement to prevent damage to the body wall in which the device is engaged, subsequently to return to that original engaging position when the migratory force is removed. "Lumen" as that term is used herein is intended to include any such body wall adjacent which a medical implant may be placed.

Accordingly, while the invention is illustrated and described herein with reference to specific embodiments, the claims which follow are not intended to be limited to the details shown but rather are intended to be construed to encompass all such forms and variants of the invention which may be made by those skilled in the art which forms and variants are nevertheless within the true spirit and scope of this invention.

What is claimed:

1. A barb-implant combination for retaining an implant in a body lumen, the barb-implant combination comprising at least a first barb element constructed from a first material and adapted to be attached to or comprise a part of the implant and a second barb element adapted to engage a lumen in which the implant is adapted to be deployed, said second barb element comprising a second material different from the first material, wherein the second material is a shape memory material which yields by undergoing a stress induced phase change, said second barb element being adapted to resist any force tending to displace the implant to which the first barb element is attached when that force is below a pre-determined force limit and also being adapted to yield to any force tending to displace the implant when that force exceeds the pre-determined force limit, wherein the first barb element is secured to the implant by a crimp tube in which a plurality of implant elements are also secured, said plurality of implant elements comprising a first wire having a first wire end extending into and terminating in a first end of the crimp tube and a second wire having a second wire end extending into and terminating in a second end of the crimp tube, wherein the first wire end and the second wire end are secured within the crimp tube such that the crimp tube wraps around the first wire end and the second wire end.

2. The barb-implant combination as recited in claim 1, wherein at least one part of the barb is comprised of Nitinol.

3. The barb-implant combination as recited in claim 1 wherein the first barb element is an integral part of the implant.

4. The barb-implant combination as recited in claim 1 wherein the first barb element is secured to the implant.

5. The barb-implant combination as recited in claim 1 wherein the first and second implant elements secured in said crimp tube are adjacent ends of the first implant segment and the second implant element which includes an open cell structure adapted to be deployed in an aorta adjacent a juncture with renal arteries.

6. A method of affixing an implant in a body lumen such that axial force on the implant is resisted below a pre-determined force limit and not resisted above that limit, the method comprising:

(a) providing the implant with at least a first barb element constructed from a first material and adapted to be attached to or comprise a part of the implant and a second barb element adapted to engage a lumen in which the implant is adapted to be deployed, said second barb element comprising a second material different from the first material, wherein the second material is a shape memory material which yields by undergoing a stress induced phase change, said second barb element being adapted to resist any force tending to displace the implant to which the first barb element is attached when that force is below the pre-determined force limit and also being adapted to yield to any force tending to displace the implant when that force exceeds the pre-determined force limit, wherein the first barb element is secured to the implant by a crimp tube in which a plurality of implant elements are also secured, said plurality of implant elements comprising a first wire having a first wire end extending into and terminating in a first end of the crimp tube and a second wire having a second wire end extending into and terminating in a second end of the crimp tube, wherein the first wire end and the second wire end are secured within the crimp tube such that the crimp tube wraps around the first wire end and the second wire end;

(b) locating said implant in the body lumen; and (c) affixing said implant to the body lumen thereto by engagement of the second barb element such that when the implant is translated in a direction toward the second barb element, the second barb element bends toward the first barb element when the implant experiences a force exceeding the predetermined limit.

7. An implant adapted to be affixed to a body lumen such that an axial force on the implant is resisted below a pre-selected implant force limit and not resisted above that force limit, the implant comprising:

a first wire having a first wire end;

a second wire having a second wire end;

a barb element having a first barb segment and a second barb segment, the first barb segment element constructed from a first material, the second barb segment comprising a second material different from the first material, the second material being adapted to resist any force is tending to displace the implant to which the barb element is attached when that force is below a pre-determined force limit and also being adapted to yield to any force tending to displace the implant when that force exceeds the pre-determined force limit, wherein the second material is shape memory material which yields by undergoing a stress induced phase change; and a crimp tube having a first crimp tube end into which the first wire end and the first barb segment are inserted and a second crimp tube end into which the second wire end is inserted, such that the first wire end, the first barb segment, and the second wire end are secure within the crimp tube such that the crimp tube wraps around the first wire end, the first barb segment, and the second wire end.

8. A barb-implant combination for retaining an implant in a body lumen, the barb-implant combination comprising a barb element having at least a first barb segment extending in a first direction and adapted to be attached to or comprise a part of the implant and to not engage the body lumen and a second barb segment extending in a second direction generally opposite the first direction and adapted to engage a lumen in which the implant is adapted to be deployed, said first barb segment constructed from a first material and said second barb segment comprising a second material different from the first material, wherein the second material is a shape memory material, the second barb segment being adapted to resist any force tending to displace the implant to which the first barb segment is attached when that force is below a pre-determined force limit and the second barb segment also being adapted to yield to any force tending to displace the implant when that force exceeds the pre-determined force limit by flipping back toward the first barb segment such that the second barb segment extends generally toward the first direction.

9. The barb-implant combination according to claim 8, further comprising a crimp tube coupled to the first barb segment and to the implant, the crimp tube retaining the barb to the implant.

* * * * *